United States Patent [19]

Lafon

[11] Patent Number: 4,927,855

[45] Date of Patent: May 22, 1990

[54] LEVOROTATORY ISOMER OF BENZHYDRYLSULFINYL DERIVATIVES

[75] Inventor: Louis Lafon, Paris, France

[73] Assignee: Laboratoire L. Lafon, Maisons Alfort, France

[21] Appl. No.: 7,720

[22] Filed: Jan. 28, 1987

[30] Foreign Application Priority Data

Jan. 31, 1986 [FR] France .................. 86 01337

[51] Int. Cl.$^5$ .................. A61K 31/165; C07C 147/14; C07C 103.22

[52] U.S. Cl. .................. 514/618; 514/133; 514/139; 514/162; 562/430; 560/11; 560/15

[58] Field of Search .................. 564/162, 133, 139; 514/618

[56] References Cited

U.S. PATENT DOCUMENTS

4,177,290 12/1979 Lafon .................. 514/618

FOREIGN PATENT DOCUMENTS

0097071 12/1983 European Pat. Off. .......... 564/162

*Primary Examiner*—Floyd D. Higel
*Attorney, Agent, or Firm*—Kuhn and Muller

[57] ABSTRACT

The levorotatory isomer of benzhydrylsulfinylacetamide has useful pharmaceutical activity on the central nervous system, particularly as an antidepressant and stimulant in the treatment of hypersomnia and Alzheimer's disease.

6 Claims, No Drawings

LEVOROTATORY ISOMER OF BENZHYDRYLSULFINYL DERIVATIVES

The present invention relates to the levorotatory derivative of benzhydrylsulfinylacetamide, the method for its preparation and its use in therapy, especially as an antidepressant and stimulant for the central nervous system (CNS), the said derivative being useful in particular in the treatment of hypersomnia on account of its arousing effects.

It is known that French Pat. No. 78 05 510 (publication No. Fr-B-2 385 693) describes the racemate (±)-benzhydrylsulfinylacetamide, which has the code number CRL 40 476 and the following structural formula:

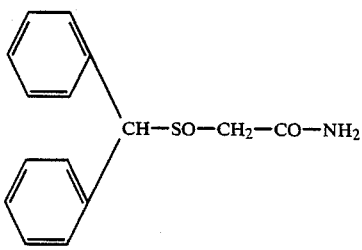

as a product (see Example 1 of the said French patent) and as stimulant for the central nervous system (CNS).

It is also known that, in Patent Document EP-A-No. 0 097 071, the neuropsychopharmacological properties of the racemate were compared with those of the analogs of the formula:

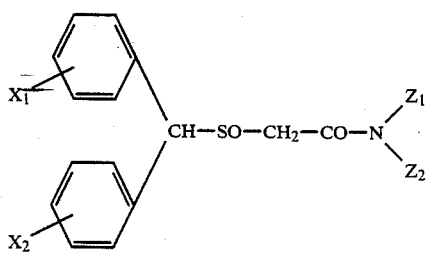

in which:
$X_1$ and $X_2$, which can be identical or different, each represent, H, Cl or F, $Z_1$ represents $CH_3$, $CH_2Ch_3$, $CH(CH_3)_3$, it also being possible for $Z_1$ to represent a hydrogen atom when at least one of the symbols $X_1$ and $X_2$ is different from H, and $Z_2$ represents H, it being possible for $NZ_1Z_2$, considered together, to represent a piperidino or morpholino group, which act on the CNS as sedatives in some cases and as stimulants in others (see especially Table I on page 3 and Table IV on page 4 of the said European patent document).

It has now been found that the levorotatory compound (−)-benzhydrylsulfinylacetamide (Code no.: CRL 40 982) has valuable therapeutic properties compared with the racemate (±)-benzhydrylsulfinylacetamide (Code no.: CRL 40 476) and with the dextrorotatory compound (+)-benzhydrylsulfinylacetamide (Code no.: CRL 40 983). Surprisingly, it has been found that the metabolism of the levorotatory compound in the organism is different form that of the racemate and the dextrorotatory compound and that the levorotatory compound is particularly valuable in the treatment of hypersomnia and Alzheimer's disease.

According to the invention, a novel industrial product is recommended which is useful in therapy and belongs to the family of the benzylhydrylsulfinyl derivatives, the said product being (−)-benzhydrylsulfinylacetamide.

This levorotatory compound cannot be prepared by isolation from the corresponding racemic amide. However, it can be prepared by chemical synthesis from a precursor of the amide, according to a method known per se, by the application of conventional reaction mechanisms.

The method of preparation recommended according to the invention consists in:

(1°) reacting (±)-benzhydrylsulfinylacetic acid with (−)-α-methylbenzylamine to give the (−)-benzhydrylsulfinylacetate of (−)-α-methylbenzylamine (the reaction advantageously being carried out in the presence of a small excess of amine relative to the stoichiometric conditions, and more particularly with a molar ratio amine/acid of between 1.02/1 and 1/15/1 and preferably of between 1.05/1 and 1.10/1), (2°) converting the resulting (−)-benzhydrylsulfinylacetate salt of (−)-α-methylbenzylamine to (−)-benzhydrylsulfinylacetic acid [the conversion advantageously being carried out by hydrolysis in an acid medium, the solvent being warm water (especially water at 30°–45° C.], and (3°) subjecting the resulting (−)-benzhydrylsulfinylacetic acid to an amidation reaction with gaseous ammonia.

The amidation of stage (3°) is advantageously carried out in 2 steps, namely:

(3a) esterification of the (−)-benzhydrylsulfinylacetic acid to a lower alkyl (−)-benzyldrylsulfinylacetate [the lower alkyl being $C_1$-$C_3$, especially isopropyl, ethyl or methyl (preferably ethyl and particularly preferably methyl)], followed by (3b) transamidation of the resulting lower alkyl (−)-benzhydrylsulfinlacetate with $NH_3$ ( the transamidation reaction preferably being carried out in a lower alcohol and particularly preferably in the alcohol corresponding to the alkyl group of the ester obtained in stage 3a), a stream of $NH_3$ being passed into the reaction medium).

(±)-Benzyhydrylsulfinylacetic acid is a known substance which is described as synthesis intermediate in Patent Document FR-B-No. 2 326 181 (m.p. (inst.)=16-4°-165° C.).

According to the invention, a therapeutic composition is recommended which contains (−)-benzhydrylsulfinylacetamide as the active ingredient, in association with a physiologically acceptable excipient. Of course, in a composition of this type, the said (−)-benzhydrylsulfinylacetamide is present in a pharmaceutically effective amount.

It is also recommended to use this levorotatory compound to obtain, on the one hand, an arousing drug to be used in human therapy for hypersomnia, and, on the other hand, a stimulating drug, and in particular a drug for inhibiting aphasia and ideomotor apraxia, to be used in therapy for Alzheimer's disease.

Further advantages and characteristics of the invention will be understood more clearly from the following description of (i) preparation examples and (ii) results of comparative neurophyschopharmacological tests. These data, which in no way imply a limitation, are given by way of illustration.

PREPARATION I

Preparation of (−)-benzhydrylsulfinylacetamide (Example 1; Code no.: CRL 40 982)

(a) (−)-Benzhydrylsulfinylacetate of (−)-α-methylbenzylamine 13 g (0.108 mol) of (−)-α-methylbenzylamine are added to a suspension of 27.4 g (0.1 mol) of (±)-benzhydrylsulfinylacetic acid (m.p. (inst.)=164°-165° C.; Code no.: CRL 40 467) in 500 ml of water; the mixture is filtered hot, the filtrate is cooled and the product is filtered off and recrystallized twice from 300 ml of water to give 17 g (yield: 42%) of the (−)-benzhydrylsulfinylacetate of (−)-α-methylbenzylamine. M.p. (inst.)=148°-150° C.

(b) (−)-Benzhydrylsulfinylacetic acid the (−)-benzhydrylsulfinylacetate of (−)-α-methylbenzylamine (17 g) obtained in this way is dissolved in 800 ml of warm water (30°-40° C.) and then acidified with 7 ml of concentrated hydrochloric acid (12N HCl, $d=1.19$ g/cm$^3$). The mixture is filtered cold and the precipitate is washed with water and dried to give the expected (−)-benzhydrylsulfinylacetic acid with a yield of about 100%.

M.p. (inst.)=185°-188° C.
$\alpha_D^{20°\ C.}=-35°$ (in a 1% solution in CH$_3$OH).

(c) Methyl (−)-benzhydrylsulfinylacetate

A suspension of 16.45 g (0.06 mol) of (−)-benzhydrylsulfinylacetic acid in 300 ml of water is treated at 20° C. with 16.8 g (0.2 mol) of sodium bicarbonate and 18.8 ml (0.21 mol) of methyls sulfate, with stirring, the mixture is stirred for 16 to 18 hours at 20° C. and filtered and the material on the filter is washed with water and dried to give methyl (−)-benzhydrylsulfinylacetate with a yield of 85%.

M.p. (inst.)=109°-110° C.
$\alpha_D^{20°\ C.}=-22.5°$ (in a 4% solution in CH$_3$OH).

(d) CRL 40 982

A dry stream of NH$_3$ gas is passed at room temperature into a solution of 100 ml of methanol containing 8.6 g (0.03 mol) of methyl (−)-benzhydrylsulfinylacetate. NH$_3$ introduced in this way is reacted with the solution for 5 h, with stirring. The methanol is evaporated off, the evaporation residue is taken up in ether and the product is filtered off and recrystallized from ethanol to give CRL 40 982 with an overall yield of 32%. This product is in the form of white crystals which are soluble in alcohols and acetone and insoluble in water and ether.

M.p. (inst.)=153°-154° C.
$\alpha_D^{20°\ C.}=-20°$ (in a 2% solution in CH$_3$OH),

PREPARATION II

Preparation of (+)-benzhydrylsulfinylacetamide (Comparison product CP1; Code no.: CRL 40 983)

The following are obtained successively using the procedure indicated in Preparation I above but replacing the (−)-α-methylbenzylamine with (+)-α-methylbenzylamine.

(a) the (+)-benzhydrylsulfinylacetate of (+)-α-methylbenzylamine;
M.p. (inst.)=148°-150 C.;

(b) (+)-benzhydrylsulfinylacetic acid;
M.p. (inst.)=190°-191° C.,
$\alpha_D^{20°\ C.}=+45°$ (in a 1% solution in CH$_3$OH);

(c) methyl (+)-benzylhydrylsulfinylacetate;
M.p. (inst.)=109°-110° C.,
$\alpha_D^{20°\ C.}=+22.2°$ (in a 4% solution in CH$_3$OH);
and then (d) CRL 40 983;
M.p. (inst.)=153°-154° C.,
$\alpha_D^{20°\ C.}=+22°$ (in a 2% solution in CH$_3$OH).

The comparative tests which were undertaken with the levorotatory derivative according to the invention (Ex. 1; Code no.: CRL 40 982), the dextrorotatory derivative (CP1; Code no.: CRL 40 983) and the corresponding racemate (CP2; Code no.: CRL 40 476) have been summarized below. Unless indicated otherwise, the 3 products studied in these tests were administered intraperitoneally as a suspension in an aqueous solution of gum arabic, in a volume of 20 ml/kg to male mice and in a volume of 5 ml/kg to male rats.

A—TOXICITY

In male mice, the LD$_O$ (maximum non-lethal dose) by intraperitoneal administration is found to be greater than or equal to 512 mg/kg for the dextrorotatory compound and the racemate, whereas the LD$_{30}$ of the levorotatory compound is of the order of about 512 mg/kg.

In summary, CRL 40 982 is more toxic than CRL 40 983 (CP1) and CRL 40 476 (CP2). The fact that the toxicity of CRL 40 982 is greater than that of the other two products does not present a problem since the levorotatory compound still has a sufficiently wide useful range of non-lethal concentrations. Here, the fact that CRL 40 982 is more toxic than the other two products indicates that it is more active.

B—BEHAVIOR IN RATS

In male mice, CRL 40 982, CRL 40 983 and CRL 40 476 have stimulant effects; in male rats, on the other hand, it is found that CRL 40 982 and CRL 40 983 do not have stimulant effects while the racemate (CRL 40 476) (i) is a stimulant and (ii) has a mydriatic action at all the doses used, the levorotatory and dextrorotatory isomers being devoid of this mydriatic action when administered on their own:

at a dose of 128 mg/kg, CRL 40 476 causes excitation with an increase in the fear ration for 2 h, exophthalmos for 1 h and mydriasis for 1 for 2 h;

at a dose of 32 mg/kg, CRL 40 476 causes excitation (transient, lasting 0.5 h) with an increase in the fear reaction for 1 h, exophthalmos for 0.5-1 h and mydriasis for 1-2 h;

at a dose of 8 mg/kg, CRL 40 476 causes exophthalmos for 0.5-1 h and mydriasis for 0.5 h;

at a dose of 2 mg/kg, CRL 40 476 induces transient mydriasis appearing 1 h after administration, whereas at a doses of 64 mg/kg, 16 mg/kg, 4 mg/kg and 1 mg/kg, CRL 40 982 and CRL 40 983 cause behavior, reactivities and variations in the rectal temperature and pupil diameter which are substantially comparable to those of the control group.

C—MOTOR ACTIVITY IN MICE

The mice (6 per dose, 18 control animals) receive CRL 40 476, CRL 40 982 or CRL 40 983 four hours before being placed in an actimeter, where their motility is recorded for 30 minutes. It is found that, at doses of 128 mg/kg and to a lesser extent 64 mg/kg, the three substances used cause an increase in the motor activity four hours after their administration. However, the hyperactivity induced by CRL 40 982 and CRL 40 983 reaches a level and a degree of statistical significance which are greater than those due to CRL 40 476, especially at the highest dose used (128 mg/kg).

In summary, under the experimental conditions (intraperitoneal administration of the substances four hours before the test), CRL 40 982 shows a stimulant effect equal in intensity to that observed with CRL 40 983, while the hyperactivity induced by CRL 40 476 is less than that obtained with either CRL 40 982 or CRL 40 983.

D—PHARMACOKINETIC STUDY

In the organism, CRL 40 476 is partially converted to (±)-benzhydrylsulfinylacetic acid (CRL 40 467) of the structural formula:

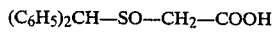

which is used as the starting material for the synthesis of the optical isomers CRL 40 982 and CRL 40 983.

Now, this metabolite is found to be inactive. In fact, CRL 40 467, administered intraperitoneally to male mice at doses of 1024 mg/kg, 512 mg/kg, 256 mg/kg, 128 mg/kg and 64 mg/kg, induces the appearance of brief sedation (with a duration less than or equal to about 50–60 minutes) and does not cause the death of any of the animals treated. Its neuropsychopharmacological study did not reveal any psychotropic activity.

to distinguish CRL 40 982 from the racemic and dextrorotatory compounds, a kinetic study of the metabolism was undertaken on dogs (group of four animals). In a randomized crossover procedure, each animal received the following at the rate of one oral administration per week: 2 administrations of CRL 40 476 (for assessment of the variations within individuals), 1 administration of CRL 40 982 and 1 administration of CRL 40 983. Following each of these administrations, the kinetics of the CRL 40 476 and CRL 40 467 present in the plasma were determined (without looking to see whether these two products were in the racemic, levorotatory and/or dextrorotatory form, because of the difficulties associated with determining the optical rotation of each of the optical isomers in a biological medium).

The dose administered for each of the test substances CRL 40 476, CRL 40 982 and CRL 40 983 was 30 mg/kg.

After administration of CRL 40 476, the said CRL 40 476 and its metabolite, CRL 40 467, are found in the plasma.

After the administration of CRL 40 982, the following are found in the plasma: the said CRL 40 982, which will be characterized and determined as being CRL 40 476 by way of convenience, in view of what has been said above, and a metabolite which will be characterized and determined as being CRL 40 467.

Likewise, after administration of CRL 40 983, the 2 corresponding products in the plasma will be characterized and determined as being CRL 40 476 and CRL 40 467.

The curves of the plasma concentrations of the said CRL 40 476 and CRL 40 467 as a function of time are plotted from time $T=2$ to time $T=+9$ h after administration of the CRL 40 476, CRL 40 982 and CRL 40 983. The areas under the curves ($AUC_o^{+9h}$) are then calculated. The results obtained are recorded in Table I below. They show this:

(a) after administration of CRL 40 476 and CRL 40 983, the $AUC_o^{+9h}$ of CRL 40 476 are not statistically different, whereas, after administration of CRL 40 982, the $AUC_o^{+9h}$ of CRL 40 476 is approximately twice the $AUC_o^{+9h}$ of CRL 40 476 which each result from the administration of CRL 40 476 and CRL 40 476 and CRL 40 983; and (b) the quantity of CRL 40 467 produced after administration of CRL 40 983 is very large (83.12 mg.$l^{-1}$.h), whereas the quantity produced after administration of CRL 40 982 is very small (8.69 mg.$l^{-1}$.h).

The value of CRL 40 982 according to the invention is in the fact that only a small proportion of this product is converted to inactive CRL 40 467, whereas a very high proportion of the corresponding dextrorotatory derivative is metabolized to CRL 40 467. In summary, the levorotatory compound CRL 40 982 has a better bioavailability than the racemic compound CRL 40 476 and the dextrorotatory compound CRL 40 983, in view of the small quantity of inactive metabolite which it produces in the organism.

These pharmacokinetic results were confirmed on rabbits and mice. An immunostimulant effect was also observed in vitro for CRL 40 982.

E—CLINICAL TRIALS

In human clinical trials, it was found that the elimination half-life of CRL 40 982 is relatively long (about 10 h), making it possible to obtain good results on adults with 1 to 2 administrations per day.

In the course of the clinical trials, CRL 40 982 was found to act in the short term as a purely hypnogenic, antiarousing substance and in the long term as an arousing substance useful for hypersomnia. Furthermore, in both the short and long term, CRL 40 982 was shown to be particularly active towards the symptoms of dementia and loss of memory (especially in the elderly).

Administered once or twice a day in the form of tablets or gelatin capsules each containing 50 to 100 mg of CRL 40 982, this product has a different stimulant neuropsychopharmacological profile from that of the amphetamines and tricyclic antidepressants and is useful of depressions, hypersomia and in particular Alzheimer's disease (improvement of the symptoms of dementia, memory disorders, aphasia and ideomotor apraxia).

TABLE I

PHARMACOKINETIC STUDY ON DOGS
MEASURMENT OF THE AREAS UNDER THE CURVES ($AUC_o^{+9h}$)

| Product administered | Code no. | $AUC_o^{+9h}$ CRL 40 476 (a) | | $AUC_o^{+9h}$ CRL 40 467 (a) | |
|---|---|---|---|---|---|
| CP2 | CRL 40 476 | 46.76 ± 6.95 ]** | | 35.12 ± 6.93 ]** | |
| Ex. 1 | CRL 40 982 | * [ 97.22 ± 12.58 ] | n.s. | [ 8.69 ± 1.22 ] | * |
| CP1 | CRL 40 983 | 50.94 ± 8.77 | ** | 83.12 ± 21.66 | |

Notes
(a) in $mg.l^{-1}.h$
* statistically significant difference ($p < 0.1$)
** statistically very significant difference ($p < 0.01$)
n.s. statistically non-significant difference

What is claimed is:

1. (−)-Benzhydrylsulfinylacetamide.

2. A method for the treatment of hypersomnia, which comprises administering, to a patient in need of such a treatment, an effective amount of a pharmaceutical composition consisting essentially of (−)-benzhydrylsulfinylacetamide as an arousing agent.

3. A method for the treatment of Alzheimer's disease, which comprises administering, to a patient in need of such a treatment, an effective amount of a pharmaceutical composition consisting essentially of (−)-benzylhydrylsulfinylacetamide as a central nervous system stimulant.

4. A therapeutic composition comprising an amount (−)-benzhydrylsulfinylacetamide in combination with a physiologically acceptable excipient effective to serve as an arousing agent.

5. A therapeutic composition comprising an amount effective as a central nervous system stimulant of (−)-benzhydrylsulfinylacetamide in combination with a physiologically acceptable excipient.

6. A pharmaceutical composition useful in therapy as a central nervous system stimulant consisting essentially of (−)-benzhydrylsulfinylacetamide in combination with a physiologically acceptable medium.

* * * * *